(12) United States Patent
Hong et al.

(10) Patent No.: US 8,735,106 B2
(45) Date of Patent: May 27, 2014

(54) IMMOBILIZATION OF PSICOSE-EPIMERASE AND A METHOD OF PRODUCING D-PSICOSE USING THE SAME

(75) Inventors: Young Ho Hong, Gwangmyeong-si (KR); Jin Ha Kim, Bucheon-si (KR); Sung Bo Kim, Seoul (KR); Jung Hoon Kim, Seoul (KR); Young Mi Lee, Bucheon-si (KR); Seung Won Park, Yongin-si (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/499,504

(22) PCT Filed: Sep. 1, 2010

(86) PCT No.: PCT/KR2010/005902
§ 371 (c)(1),
(2), (4) Date: Jun. 13, 2012

(87) PCT Pub. No.: WO2011/040708
PCT Pub. Date: Apr. 7, 2011

(65) Prior Publication Data
US 2012/0244580 A1    Sep. 27, 2012

(30) Foreign Application Priority Data

Sep. 30, 2009 (KR) .................. 10-2009-0092784
Dec. 2, 2009 (KR) .................. 10-2009-0118465

(51) Int. Cl.
C12P 19/02 (2006.01)
C12P 7/26 (2006.01)
C12N 9/90 (2006.01)
C12N 1/20 (2006.01)
C12N 15/00 (2006.01)

(52) U.S. Cl.
USPC ...... 435/105; 435/148; 435/252.1; 435/252.3; 435/233; 435/320.1; 536/23.2

(58) Field of Classification Search
None
See application file for complete search history.

(56) References Cited

U.S. PATENT DOCUMENTS

2005/0250937 A9    11/2005  Li et al.
2010/0204346 A1     8/2010  Okuma et al.

FOREIGN PATENT DOCUMENTS

| EP | 1357182 A1 | 10/2003 |
| EP | 1956088 A1 | 8/2008 |
| WO | 2008/142860 A1 | 11/2008 |
| WO | 2011/040708 A2 | 4/2011 |

OTHER PUBLICATIONS

Oh et al. Tagatose: properties, applications and biotechnological processes, Appl Microbiol Biotechnol (2007), 76: 1-8.*
GenBank Accession No. NP_355915, Oct. 3, 2001.
Itoh, H. et al., "Preparation of D-Psicose from D-Fructose by Immobilized D-Tagatose 3-Epimerase," *Journal of Fermentation and Bioengineering* 80(1):101-103, 1995.
Kim, H-J. et al., "Characterization of an *Agrobacterium tumefaciens* D-Psicose 3-Epimerase That Converts D-Fructose to D-Psicose," *Applied and Environmental Microbiology* 72(2):981-985, 2006.

* cited by examiner

*Primary Examiner* — Iqbal H Chowdhury
(74) *Attorney, Agent, or Firm* — Seed IP Law Group PLLC

(57) ABSTRACT

The present invention relates to a method of successively producing D-psicose from D-fructose or D-glucose by using a psicose-epimerase derived from *Agrobacterium tumefaciens* which is expressed in a food safety form.

13 Claims, 6 Drawing Sheets

IMMOBILIZATION OF PSICOSE-EPIMERASE AND A METHOD OF PRODUCING D-PSICOSE USING THE SAME

CROSS-REFERENCES TO RELATED APPLICATIONS

This application is a U.S. national stage application filed under 35 U.S.C. §371 of International Patent Application PCT/KR2010/005902, accorded an international filing date of Sep. 1, 2010, which claims priority to Korean (KR) Patent Application No. 10-2009-0092784 filed Sep. 30, 2009, and Korean (KR) Patent Application No. 10-2009-0118465 filed Dec. 2, 2009.

STATEMENT REGARDING SEQUENCE LISTING

The Sequence Listing associated with this application is provided in text format in lieu of a paper copy, and is hereby incorporated by reference into the specification. The name of the text file containing the Sequence Listing 200198_404USPC_SEQUENCE_LISTING_ST25.txt. The text file is 8 KB, was created on Mar. 30, 2012, and is being submitted electronically via EFS-Web.

TECHNICAL FIELD

The present invention relates to a method of successively producing D-psicose from D-fructose or D-glucose by using a psicose-epimerase derived from *Agrobacterium tumefaciens* which is expressed in a food safety form.

BACKGROUND ART

D-psicose has been widely used as a functional sweetener which has a sweet taste similar to sugar but is an ultralow-energy monosaccharide sugar. In particular, D-psicose is known as a "rare sugar" because it is rarely found in nature, and even when found, only in small amounts.

D-psicose is an epimer of D-fructose, and the sweetness intensity and kinds thereof are quite similar to those of D-fructose. However, contrary to D-fructose, since when absorbed into the body, D-psicose is rarely metabolized, it has almost zero calories. Further, due to its action to alleviate abdominal obesity by suppressing enzyme activities regarding to lipid synthesis, D-psicose can be used as an effective ingredient of diet foods. In addition, while sugar alcohols widely used as a substitute for sugar have a problem of causing side effects such as diarrhea when taken in excessive amounts, D-psicose has almost no side effects (Matsue, T., Y. Baba, M. Hashiguchi, K. Takeshita, K. Izumori, and H. Suzuki. 2001. Dietary D-psicose, a C-3 epimer of D-fructose, suppresses the activity of hepatic lipogenic enzymes in rats. Asia Pac. J. Clin. Nutr. 10:233-237; Matsuo, T., and K. Izumori. 2004. D-psicose, a rare sugar that provides no energy and additionally beneficial effects for clinical nutrition. Asia Pac. J. Clin. Nutr. 13:S127).

Due to such reasons, D-psicose is getting the spotlight in the food industry field as a diet sweetener, and thus, there is a growing need to develop a method of producing D-psicose efficiently.

Conventional methods of producing D-psicose by using a psicose-epimerase had been focused to develop an epimerization process of D-psicose from D-fructose by using a recombinant enzyme massively expressed in a recombinant E. coli or a host cell comprising the same. However, the biotechnological production of D-psicose using such a recombinant E. coli is unsuited for the production of D-psicose as a food material in terms of food safety. In order to produce D-psicose suitable to be used as a food material, it is required to develop a mass production method using a psicose-epimerase expressed in a host cell which is a GRAS (Generally Recognized As Safe) strain as well as a strain capable of being industrially mass producing, or using a host comprising the same.

GRAS is granted for substances that are generally recognized to be safe when experts qualified by scientific training and experience evaluate their safety through scientific procedures under the conditions of their intended use. GRAS is a unique system only implemented in USA, but its importance and necessity has been recognized internationally as well as in USA. Therefore, people are paying attention to the development of GRAS.

Meanwhile, for the industrial production of D-psicose, it is required to develop a method of producing D-psicose from a more inexpensive substrate. Currently, due to a high substrate specificity of a psicose-epimerase, only expensive D-fructose is used as a substrate for the production of D-psicose.

DISCLOSURE OF INVENTION

Technical Problem

The present invention has been actively studied to mass produce D-psicose which can be used as a food material, and found that the successive production of D-psicose from D-fructose or D-glucose can be achieved by using immobilization for providing stable environment for enzymatic activation for the industrially mass production of D-psicose and using a D-glucose isomerase along with a psicose-epimerase.

An object of the present invention is to provide a psicose-epimerase in a food safety form for the preparation of D-psicose which can be used as a food material.

Another object of the present invention is to provide a method of successively producing D-psicose from D-glucose or D-fructose by using a psicose-epimerase and a D-glucose isomerase in an immobilized food safety form.

Technical Solution

The present invention provides a method of preparing D-psicose from D-fructose by using a psicose-epimerase derived from *Agrobacterium tumefaciens* which is expressed in a GRAS strain.

The method of the present invention comprises the steps of: expressing a psicose-epimerase derived from *Agrobacterium tumefaciens* in a GRAS strain; and preparing D-psicose from D-fructose by using the expressed psicose-epimerase.

The method of the present invention may also comprise the steps of: separating a psicose-epimerase from the culture of a GRAS strain capable of expressing a psicose-epimerase derived from *Agrobacterium tumefaciens*; and preparing D-psicose from D-fructose by using the separated psicose-epimerase.

The GRAS strain expressing a psicose-epimerase derived from *Agrobacterium tumefaciens* can be a strain transformed with a recombinant expression vector including a gene encoding the aforementioned enzyme.

The psicose-epimerase used in the preparation of D-psicose according to the present invention can be in the form of being contained in a culture of the GRAS strain expressing the psicose-epimerase derived from *Agrobacterium tumefaciens* or being isolated from the culture. The GRAS strain can be a strain transformed with a recombinant expression vector including a gene encoding a psicose-epimerase. The GRAS strain can be *Corynebacterium* sp., preferably *Corynebacterium glutamicum* KCCM 11046.

It is preferable that the psicose-epimerase derived from *Agrobacterium tumefaciens* used in the method of the present invention has the amino acid sequence of SEQ ID NO: 1.

The method of preparing D-psicose according to the present invention may further comprise the step of immobilizing the psicose-epimerase onto a carrier. The carrier suitable for the present invention may include alginate, preferably sodium alginate, but is not limited thereto.

The method of preparing D-psicose according to the present invention can further comprise the steps of packing a column with the carrier on which the psicose-epimerase is immobilized and supplying the packed-bed column with a D-fructose solution.

Also, the present invention further provides a method of preparing D-psicose from D-glucose, comprising the step of immobilizing a psicose-epimerase and a D-glucose isomerase onto carriers. The carrier suitable for the present invention may include alginate, preferably sodium alginate, but is not limited thereto.

In the method as described above, the psicose-epimerase may be contained in a culture of the GRAS strain capable of expressing psicose-epimerase derived from *Agrobacterium tumefaciens* or to be isolated from the culture. The GRAS strain can be a strain transformed with a recombinant expression vector including a gene encoding psicose-epimerase. Further, the GRAS strain can be *Corynebacterium* sp., preferably *Corynebacterium glutamicum* KCCM 11046.

It is preferable that the psicose-epimerase derived from *Agrobacterium tumefaciens* used in the method of the present invention has the amino acid sequence of SEQ ID NO: 1.

In addition, the present invention further provides a method of preparing D-psicose from D-glucose, comprising the steps of: immobilizing a psicose-epimerase and a D-glucose isomerase onto carriers; packing a column with the carriers onto which the psicose-epimerase and D-glucose isomerase are immobilized; and supplying the packed-bed column with a D-glucose solution. The carriers onto which the psicose-epimerase and D-glucose isomerase are immobilized can be packed into the same column, or respectively packed into two separate columns. However, it is preferable that the carrier is packed into a separate column, and in this case, the two separate columns are mutually connected.

The present invention provides a *Corynebacterium glutamicum* KCCM 11046 strain useful for the preparation of D-psicose from D-fructose or D-glucose.

The term "food safety form" as used herein means that it is safe enough to be used as a food material. Therefore, the term "expressed in a food safety form" as used herein means that a target gene was expressed in a strain which is recognized as being safe and causing no harmful effects although it is used as a food material, for example, a GRAS strain.

In one embodiment of the present invention, a method of transforming the GRAS strain with a recombinant vector may include an electroperforation but is not limited thereto, and may be carried out using any transformation method known to those skilled in the art to which the present invention pertains.

In one embodiment of the present invention, the recombinant vector including the gene encoding the psicose-epimerase derived from *Agrobacterium tumefaciens* may include the psicose-epimerase encoding gene operatably linked to a promoter which is active in *Corynebacterium* sp. bacteria. The promoter can have one of sequences having SEQ ID NOs: 2 to 8 that have been confirmed to express a target gene more efficiently than a tac promoter in *Corynebacterium* sp. bacteria (Korean Patent Publication NO. 2006-0068505).

The term "psicose-epimerase" as used herein means a D-psicose-3-epimerase having a conversion activity of D-fructose to D-psicose.

In one embodiment of the present invention, the psicose-epimerase derived from *Agrobacterium tumefaciens* may have the amino acid sequence of SEQ ID NO: 1 or be functional fragments thereof. The functional fragment means a fragment which includes mutations by substitution, insertion or deletion or the like of some amino acids in the amino acid sequence of SEQ ID NO: 1, while having a conversion activity of D-fructose to D-psicose.

In one embodiment of the present invention, the GRAS strain may be a *Corynebacterium* sp. strain.

The *Corynebacterium* sp. strain is an industrial microorganism producing chemicals which have various uses in an animal feed, medicine, and food fields, etc. including L-lysine, L-threonine and various nucleic acids. Such a *Corynebacterium* sp. strain is a GRAS (Generally Recognized As Safe) strain and has properties of being easy for genetic manipulation and mass cultivation. Further, the *Corynebacterium* sp. strain has high stability under various process conditions, has a relatively rigid cellular wall structure as compared with other bacteria, thereby having a biological property of existing of cell mass in a stable state even under high osmotic pressure by high sugar concentration, etc.

In one embodiment of the present invention, the *Corynebacterium* sp. strain may be *Corynebacterium glutamicum*.

In one embodiment of the present invention, the GRAS strain expressing the psicose-epimerase derived from *Agrobacterium tumefaciens* may be a recombinant strain *Corynebacterium glutamicum* KCCM 11046.

The psicose-epimerase may be easily modified by mutagenesis conventionally known to those skilled in the art such as directed evolution and site-directed mutagenesis, etc. Therefore, it should be construed that recombinant enzymes having a certain extent of sequence homology, such as sequence homology of 70% or higher, preferably 80% or higher, more preferably 90% or higher to the amino acid sequence of the psicose-epimerase represented by SEQ ID NO: 1, and being expressed as an active form in the GRAS strain; and a host cell comprising the same are within the scope of the present invention.

Culture of the GRAS strain expressing the psicose-epimerase derived from *Agrobacterium tumefaciens* may be obtained by culturing the transformed bacteria in a medium and under culture conditions that are easily selected by those skilled in the art to which the present invention pertains depending on the properties of the strain. The method of culturing may include any method of culturing known to those skilled in the art, such as batch culture, continuous culture and fed-batch culture, but is not limited thereto.

The method of preparing D-psicose according to one embodiment of the present invention may comprise the step of separating the psicose-epimerase from the culture of the GRAS strain which expresses the psicose-epimerase derived from *Agrobacterium tumefaciens*.

In one embodiment of the present invention, cells separated from the culture of the strain which expresses the psicose-epimerase derived from *Agrobacterium tumefaciens* by centrifugation, filtration, etc.; or supernatant obtained by homogenizing and centrifuging the separated cells; or the psicose-epimerase which is separated and purified from the supernatant by fractionation, chromatography, etc. may be used as an enzyme for converting D-fructose to D-psicose.

In one embodiment of the present invention, the psicose-epimerase may be in the form of the cell mass in the culture or the psicose-epimerase separated from the cell mass.

In one embodiment of the present invention, the step of preparing D-psicose may further comprise the step of immobilizing the psicose-epimerase or the cell mass expressing the same onto a carrier.

Since in case of immobilizing the enzyme or the cell mass onto a carrier, there may be provided environment for maintaining the activity for a long time, the immobilization has been used in the industrial production method using an enzyme or an microorganism. The carrier which may be used for the immobilization may include alginates such as sodium alginate, but is not limited thereto.

In one embodiment of the present invention, the immobilization may be carried out by using sodium alginate as the carrier. Sodium alginate is a natural colloidal polysaccharide which is present abundantly in cell wall of algae, consists of β-D-mannuronic acid and α-L-guluronic acid, and is formed by random-1,4 links in content, and thus, it is advantageous that the cell mass or the enzymes can be stably immobilized onto it.

In one embodiment of the present invention, the immobilization may be carried out by using 1.5% to 4.0% of sodium alginate as the carrier.

In one embodiment of the present invention, the immobilization may be carried out by using 2% of sodium alginate as the carrier.

In one embodiment of the present invention, by using sodium alginate as the carrier for immobilization, the immobilization may be carried out by adding 1- to 2-fold volume of an aqueous sodium alginate solution to a sample containing the enzyme or the cell mass, dropping the resulting mixture to a 0.1 M calcium ion solution to create the enzyme or the cell mass-alginate complex in beads by using a syringe pump and a vacuum pump.

In one embodiment of the present invention, the step of immobilizing the psicose-epimerase onto the carrier may further comprise the steps of packing a column with the immobilized enzyme and supplying the packed column with a D-fructose solution.

The column to be packed with the carrier onto which the enzyme or the cell mass is immobilized and the method of packing the column with the same may be suitably and easily selected by those skilled in the art to which the present invention pertains depending on the enzyme or the cell mass, or the carrier for immobilization used.

In one embodiment of the present invention, it is possible to prepare a packed-bed column by packing the column with the immobilized enzyme. Enzymatic reaction, i.e., conversion of D-fructose to D-psicose may be carried out by supplying the packed-bed column with a D-fructose solution that is a substrate thereof.

In one embodiment of the present invention, when the packed-bed column which is packed with the cell mass including the psicose-epimerase is supplied with the D-fructose solution at a constant concentration, the epimerization reaction proceeds by the immobilized cell mass, resulting in the conversion of D-fructose to D-psicose. The converted D-psicose is subject to separation and purification by using separation columns, and then, is available as pure D-psicose.

The term "immobilization reactor" as used herein means a reactor wherein the reaction for the production of D-psicose occurs by the cell mass or the enzyme immobilized onto the carrier, or the column packed with the cell mass or the enzyme immobilized onto the carrier. Namely, the immobilization means that a substance providing biological activities, in this case, a psicose-epimerase or a D-glucose epimerase or a cell mass including the same is immobilized onto the carrier.

The term "operational stability" as used herein means that a biological reactor for the successive production of a target product such as D-psicose may be operated while maintaining a suitable level of productivity as compared with initial activity thereof, and generally, is represented by an operation period.

In one embodiment of the present invention, the column packed with the carrier onto which the cells expressing the psicose-epimerase are immobilized is supplied with 300 g/L of D-fructose at an inflow rate of 0.1 ml/min at 50° C., which makes it possible to guarantee 25 days or longer of operational stability.

The present invention further provides a method of preparing D-psicose from D-glucose, comprising the step of immobilizing a psicose-epimerase and a D-glucose isomerase onto carriers.

As described above, since D-fructose used as a substrate for the psicose-epimerase is expensive, it is required to produce D-psicose from a cheap substrate such as D-glucose for the industrial mass production of D-psicose. The D-glucose isomerase is an enzyme to convert D-glucose to D-fructose, and thus, may provide a substrate for a psicose-epimerase by converting D-glucose to D-fructose. Therefore, it is possible to produce D-psicose from D-glucose by using both of these two enzymes.

In one embodiment of the present invention, the psicose-epimerase may be the culture of the GRAS strain expressing the psicose-epimerase derived from *Agrobacterium tumefaciens*, or the cell mass or the psicose-epimerase separated from the culture.

In one embodiment of the present invention, the D-glucose isomerase may be the culture of the GRAS strain expressing the D-glucose isomerase, or the cell mass or the D-glucose isomerase separated from the culture.

In one embodiment of the present invention, the psicose-epimerase may have the amino acid sequence of SEQ ID NO: 1.

In one embodiment of the present invention, the D-glucose isomerase may be commercially available. For example, the D-glucose isomerase or the immobilized D-glucose isomerase commercially available from Novozymes A/S (Bagsvaerd, Denmark) may be used.

The D-glucose isomerase is a representative enzyme for converting D-glucose to D-fructose and is currently used for the production of fructo-oligosaccharides. Among the enzymes currently used for the industrial production, the D-glucose isomerase is one of the enzymes whose activities and mechanisms have been clearly identified.

In one embodiment of the present invention, the GRAS strain may be a strain transformed with a recombinant vector including a gene encoding the psicose-epimerase and a gene encoding the D-glucose isomerase or a strain co-transformed with recombinant vectors including each of the genes described above.

In one embodiment of the present invention, the GRAS strain may be *Corynebacterium* sp. bacterium.

In one embodiment of the present invention, the GRAS strain expressing the psicose-epimerase derived from *Agrobacterium tumefaciens* may be the recombinant strain *Corynebacterium glutamicum* KCCM 11046.

In one embodiment of the present invention, the carrier for the immobilization may be sodium alginate.

In one embodiment of the present invention, the immobilization may be carried out by using 1.5% to 4.0% of sodium alginate as the carrier.

In one embodiment of the present invention, the immobilization may be carried out by using 2% of sodium alginate as the carrier.

In one embodiment of the present invention, by using sodium alginate as the carrier for immobilization, the immobilization may be carried out by adding 1- to 2-fold volume of the aqueous sodium alginate solution to the sample containing the enzyme or the cell mass, dropping the resulting mixture to the 0.1 M calcium ion solution to create the enzyme or the cell mass-alginate complex in beads by using the syringe pump and the vacuum pump.

In one embodiment of the present invention, the gene encoding the psicose-epimerase and the gene encoding the D-glucose isomerase may be expressed in the same GRAS strain or different two GRAS strains, respectively, and the immobilization step may be carried out by immobilizing the cells of the cultured GRAS strains or a mixture of two enzymes separated from the cells onto the carriers.

In one embodiment of the present invention, the culture of the GRAS strain expressing the psicose-epimerase or the cell mass or the psicose-epimerase separated from the culture; and the D-glucose isomerase may be immobilized onto carriers, respectively.

In one embodiment of the present invention, the method of the present invention may further comprise the step of packing the column with the carrier onto which the cells or the enzymes are immobilized.

The method of preparing D-psicose from D-glucose according to the present invention may further comprise the steps of packing the column with the immobilized psicose-epimerase and D-glucose isomerase and supplying the packed column with the D-glucose solution.

In one embodiment of the present invention, the packed-bed column may be prepared by packing the column with the immobilized enzymes. The enzymatic reaction, i.e., conversion of D-glucose to D-psicose may be carried out by supplying the packed-bed column with the D-glucose solution that is a substrate thereof.

In one embodiment of the present invention, the immobilized psicose-epimerase and D-glucose isomerase may be packed into separate columns, respectively.

The column to be packed with the carrier onto which the enzymes or the cells are immobilized and the method of packing the column with the same may be suitably and easily selected by those skilled in the art to which the present invention pertains depending on the enzymes or the cell mass, or the carrier for immobilization used. In one embodiment of the present invention, it is possible to pack two separate columns with the psicose-epimerase immobilized carrier and the D-glucose isomerase immobilized carrier, respectively, connect these two columns in communication with each other to transfer D-fructose as a product of isomerization from the column packed with the D-glucose isomerase to the column packed with the psicose-epimerase, and induce the conversion reaction of the D-fructose to the D-psicose. When the D-glucose solution as a substrate is supplied to the immobilization reactor consisting of said two communicated columns, the D-glucose is converted to the D-fructose in the column packed with the D-glucose isomerase, and the D-fructose which transfers to the column packed with the psicose-epimerase is converted to the D-psicose. Thus, it is possible to obtain the D-psicose as a final product from the D-glucose.

Advantageous Effects

The method of preparing D-psicose according to the present invention can massively and successively produce D-psicose in a food safety form which may be used as a food material from D-glucose or D-fructose.

BRIEF DESCRIPTION OF DRAWINGS

FIG. 2 illustrates the results of measuring the activity of the psicose-epimerase derived from *Agrobacterium tumefaciens* by HPLC for the method according to one embodiment of the present invention, wherein

BEST MODE FOR CARRYING OUT THE INVENTION

Hereinafter, the present invention is illustrated in more detail by the following specific examples. However, these examples are for illustration and the scope of the present invention is not limited to the examples.

Measurement of Psicose-Epimerase and D-Glucose Isomerase Activities

Activities of a psicose-epimerase and a D-glucose isomerase were measured by using D-fructose and D-glucose as a substrate, respectively. The enzymes or samples containing the same were added to a 50 mM PIPES (piperazine-N, N'-bis(2-ethanesulfonic acid)) buffer (pH 8.0) containing 100 g/L of the substrates, followed by the reaction at 50° C. for an hour and the reaction was then stopped by heating the reaction at 100° C. for 5 minutes. Concentrations of D-fructose, D-glucose and D-psicose were measured by HPLC equipped with a RI (Refractive Index) detector. HPLC analysis was performed by injecting a sample into Supelcogel Pb column set at 80° C. and then passing distilled water as a mobile phase through the column at a rate of 0.5 ml/min. D-psicose was separated at a retention time of around 32 minutes, and its % conversion and productivity were calculated based on the quantitative amount of a D-psicose reference standard. For comparative analysis of enzyme activities, one unit of an enzyme was defined as the amount of the enzyme to produce 1 mole of D-psicose per minute at pH 8.0 and 50° C.

EXAMPLE 1

Figure 1:
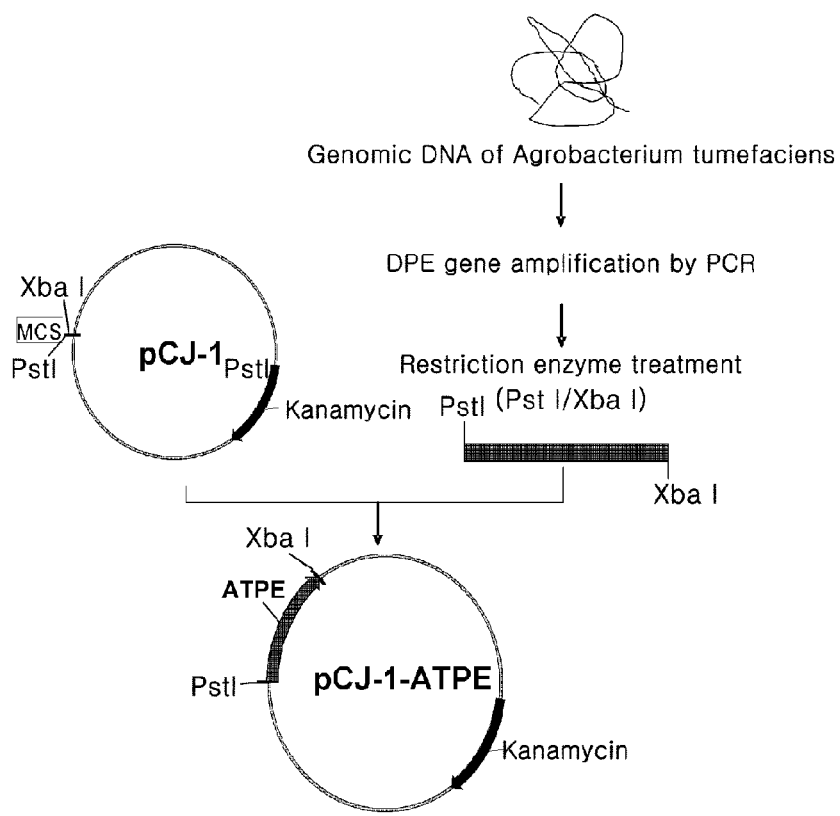
FIG. 1 schematically illustrates a process of constructing a recombinant expression vector pCJ-1-ATPE including a gene encoding a psicose-epimerase derived from *Agrobacterium tumefaciens*.

Recombinant Strain Expressing a Psicose-epimerase (1) Preparation of a Recombinant Strain The polymerase chain reaction (PCR) was carried out to amplify a gene encoding a psicose-epimerase by using a genomic DNA of *Agrobacterium tumefaciens* ATCC 33970 as a template and oligonucleotides of SEQ ID NOs: 9 and 10 with introduced PstI and XbaI restriction enzyme recognition sties, respectively, as primers. PCR conditions were as follows: after denaturation at 95° C. for 30 seconds, 26 cycles consisting of 30 seconds at 95° C., 30 seconds at 55° C. and 1 minute at 68° C., then extension at 68° C. for 10 minutes. For the mass expression of the psicose-epimerase encoded by the amplified gene, the amplified PCR product was digested with the restriction enzymes PstI and XbaI, and inserted into a shuttle vector pCJ-1 derived from *Corynebacterium* sp. bacteria (deposited with the Korean Culture Center of Microorganisms (KCCM), an international depository institution on Nov. 6 2004, under the deposit number KCCM-10611), to construct a recombinant expression vector pCJ-1-ATPE. FIG. 1 schematically shows the method of preparing the recombinant expression vector pCJ-1-ATPE including the gene encoding the psicose-epimerase derived from *Agrobacterium tumefaciens*.

The recombinant expression vector pCJ-1-ATPE was introduced into *Corynebacterium glutamicum* ATCC 13032 by transformation using electroperforation, to prepare the recombinant strain expressing the gene encoding the psicose-epimerase derived from *Agrobacterium tumefaciens*. The recombinant strain was designated *Corynebacterium glutamicum* ATPE and deposited with the Korean Culture Center of Microorganisms (KCCM, Hongje-1-dong, Seodaemum-gu, Seoul, Korea) under the deposit number KCCM 11046 on Oct. 26, 2009 under the Budapest Treaty.

(2) Expression of a Psicose-Epimerase

Figure 2A:
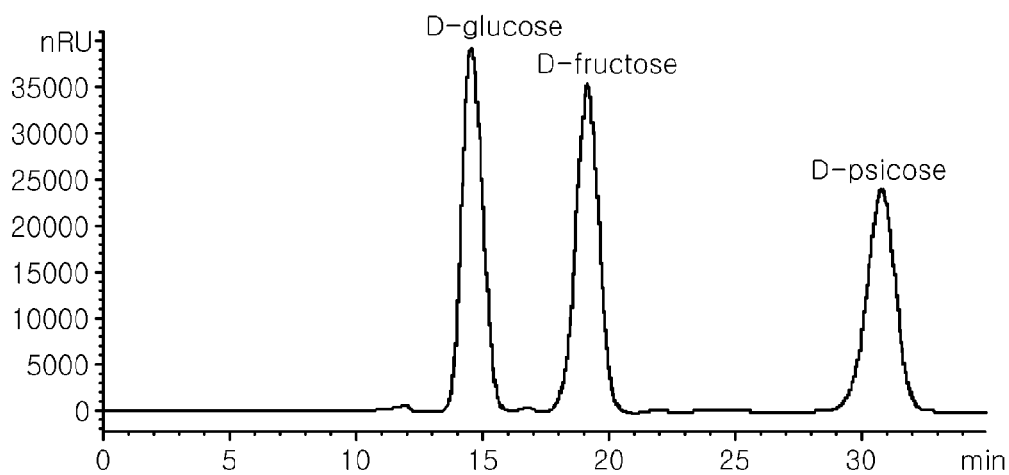
FIG. 2a shows a reference standard for each sugar.
Figure 2B:
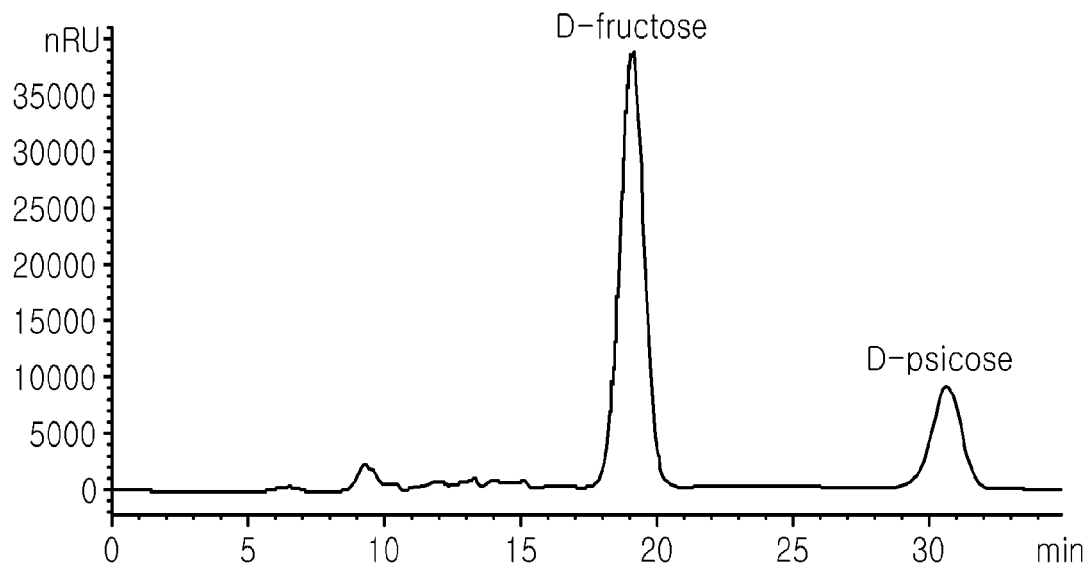
FIG. 2b shows the conversion by reaction(s).

MB media (Bacto-trypton 10 g/L, Bacto-yeast extract 5 g/L, NaCl 5 g/L, Soytone 5 g/L) including 10 µg/ml of kanamycin were inoculated with the recombinant strains obtained in the above (1), respectively, at initial concentration of OD600=0.1, followed by incubation at 30° C. for 24 hours to induce the expression of the recombination psicose-epimerase. 5 L-jar fermenter containing 3 L of a modification medium (D-glucose 80 g/L, soytone 20 g/L, $(NH_4)_2SO_4$ 10 g/L, $KH_2PO_4$ 1.2 g/L, $MgSO_4$ 1.4 g/L) including 10 µg/ml of kanamycin was inoculated with the above obtained culture at OD600=0.6, followed by incubation at 30° C. for 20 hours. In order to measure the activity of the expressed psicose-epimerase, the culture was subject to centrifugation at 8000×g for 10 minutes to harvest cells. The harvested cells were then resuspended in a 50 mM EPPS buffer (pH 8.0) (Sigma-Aldrich) and the resulting suspension was subject to ultrasonication resulting in lysis of the cells. The cell lysate was subject to centrifugation to obtain a supernatant containing the psicose-epimerase, and epimerization reaction of D-fructose was carried out by using the supernatant as an enzyme. Measuring the activity of the psicose-epimerase as described above was used in the epimerization reaction. FIG. 2*b* shows the HPLC analysis results of epimerization reaction.

EXAMPLE 2

Immobilization of a Recombinant Strain and Preparation of D-psicose (1) Immobilization of a Recombinant Strain For the mass production of D-psicose, *Corynebacterium glutamicum* ATPE (KCCM 11046) expressing the psicose-epimerase derived from *Agrobacterium tumefaciens* and prepared in the above Example 1 was immobilized onto the carrier in this example. For the immobilization of the recombinant strain, the modification medium for *Corynebacterium* used in the Example 1 was first inoculated with the recombinant strain at an initial concentration of OD600=0.6 followed by the incubation at 30° C. for 20 hours. After the completion of the incubation, the resulting culture was subject to the centrifugation to recover the cells, which were resuspended in the 50 mM EPPS buffer (pH 8.0) to be 20%. The resuspended cells of the recombinant strain were added to 2% (v/v) of an aqueous sodium alginate solution. The resulting mixture was dropped to a 100 mM $CaCl_2$ solution by using the syringe pump and the vacuum pump to create a cell-alginate complex in which the cells were trapped in sodium alginate beads.

(2) Preparation of D-Psicose by Using the Immobilized Recombinant Strain

Figure 3A:
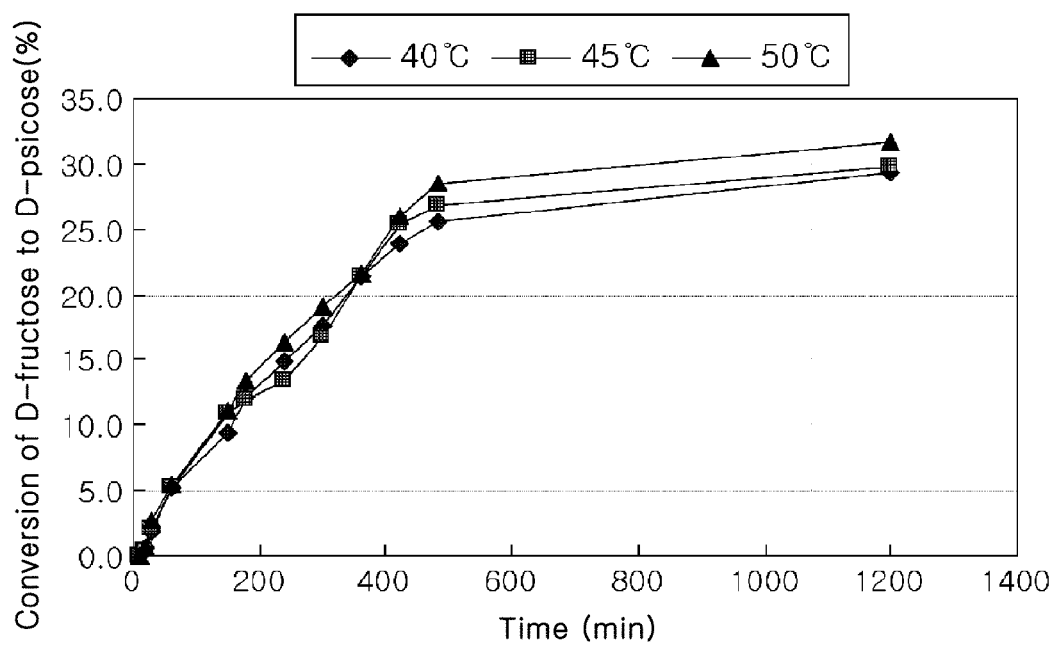
FIG. 3 illustrates % conversion of D-fructose to D-psicose by using the recombinant strain for the method according to one embodiment of the present invention under combined conditions of 100 g/L (3a), 300 g/L (3b), or 500 g/L (3c) of D-fructose, and 40° C., 45° C., or 50° C. of a reaction temperature.
Figure 3B:
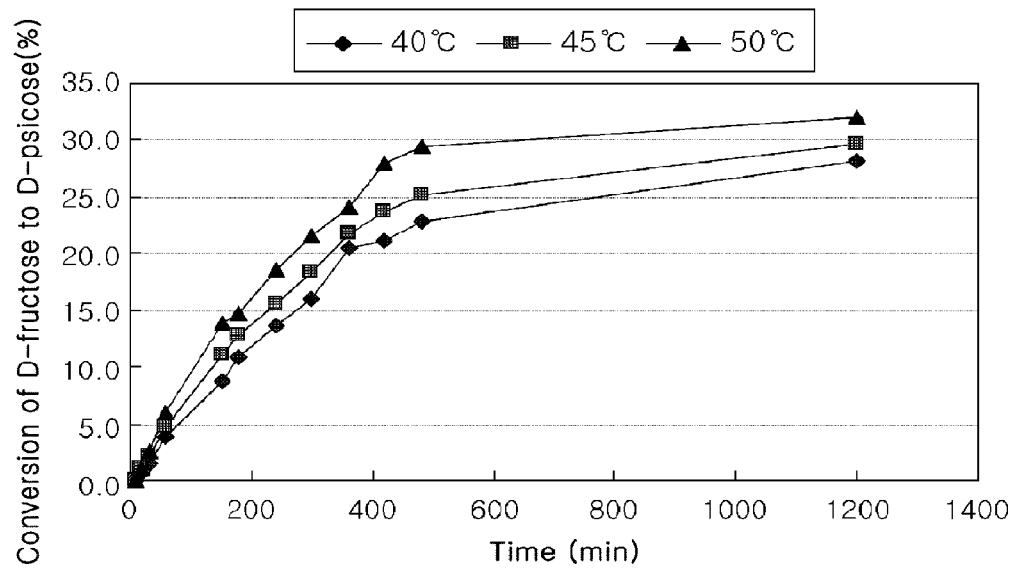
Figure 3C:
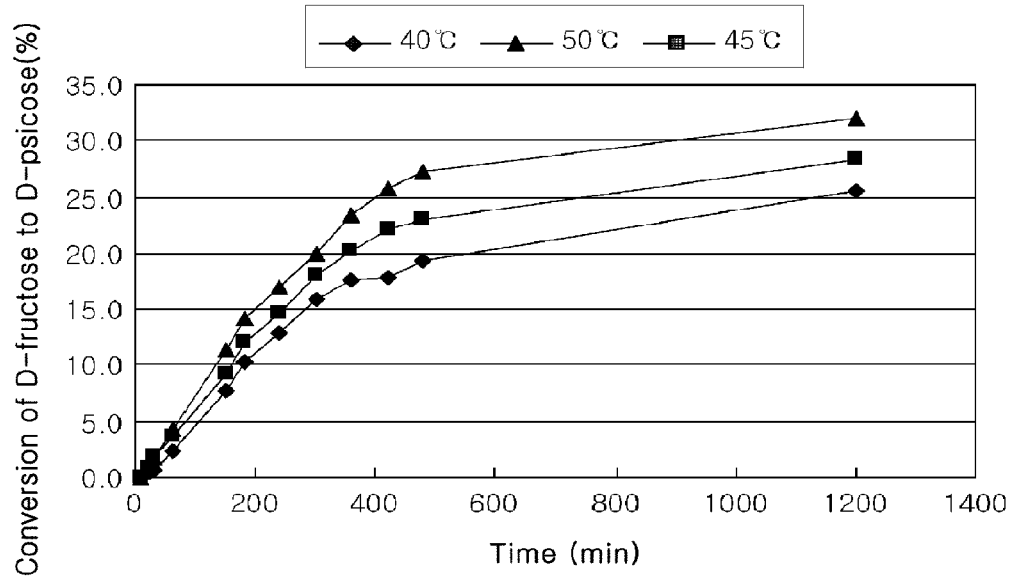

XK16 packed-bed column (16 mm×20 mm, Amersham Pharmacia) was packed with the recombinant strain immobilized onto sodium alginate in the above (1) followed by measurement of % conversion of D-fructose to D-psicose. In order to determine an optimal reaction temperature of an immobilization reactor and a substrate concentration of D-fructose, the conversion reaction of D-fructose to D-psicose was carried out under combined conditions of 40° C., 45° C. and 50° C. of reaction temperatures, and 100 g/L, 300 g/L and 500 g/L of D-fructose concentrations. According to FIGS. 3*a* to 3*c*, it was found that the best conversion is achieved at a temperature of 50° C. and 100 g/L of D-fructose concentration, and 300 g/L and 500 g/L of D-fructose concentration also give high conversion. Further, different from other D-glucose conversion reactions, the epimerization reaction for D-psicose showed low dependency on temperature.

(2-1) Productivity Depending on an Inflow Rate of D-Fructose

Figure 4:
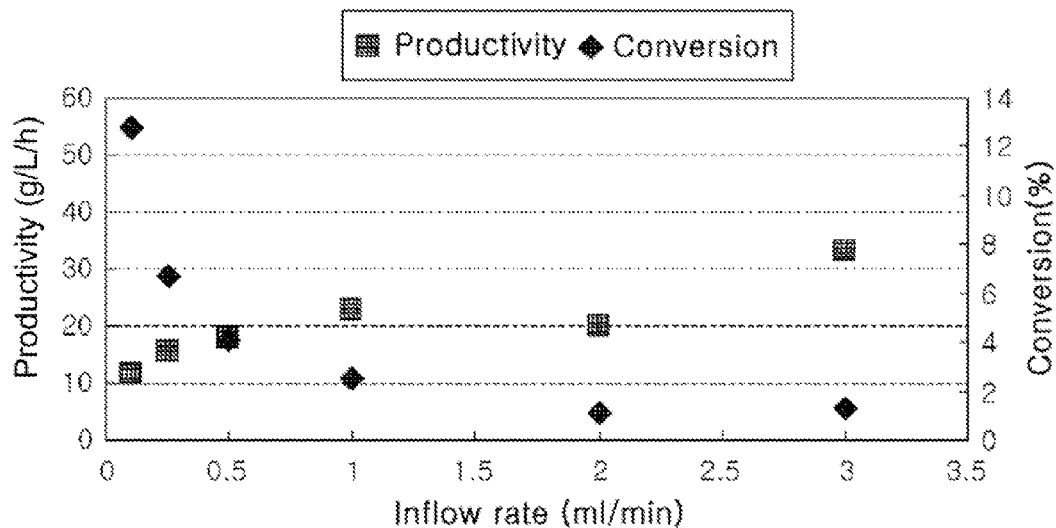
FIG. 4 illustrates the productivity of D-psicose depending on an inflow rate of D-fructose as a substrate for the method according to one embodiment of the present invention.

The XK16 packed-bed column was packed with the immobilized recombinant strain as described above followed by the measurement of the productivity of D-psicose depending on an inflow rate of D-fructose. At this time, based on the results of the above (2), the concentration of D-fructose and the reaction temperature were set at 300 g/L and 50° C., respectively. The productivity was measured by adjusting the inflow rate of D-fructose, a substrate to be 0.4, 1, 2, 4, and 8 $h^{-1}$ of space velocity (1/h). The results are shown below in Table 1 and FIG. 4.

TABLE 1

Productivity and % conversion depending on an inflow rate of D-fructose

| Inflow rate (ml/min) | D-fructose (g/l) | D-psicose (g/l) | Productivity (g/l/h) | Conversion (%) |
|---|---|---|---|---|
| 3 | 281.388 | 3.693 | 33 | 1.30 |
| 2 | 289.215 | 3.309 | 20 | 1.13 |
| 1 | 291.268 | 7.579 | 23 | 2.54 |
| 0.5 | 284.639 | 12.055 | 18 | 4.06 |
| 0.25 | 286.463 | 20.579 | 15 | 6.70 |
| 0.1 | 260.096 | 38.041 | 11 | 12.76 |

(2-2) Operational Stability

Operation was carried out at 50° C. by using the immobilized recombinant strains which were packed into the XK16 packed-bed column until specific activities thereof become 50%, respectively, in order to measure operational stability of the immobilized recombinant strains which was packed into the column. At this time, the substrate concentration of D-fructose was 300 g/L and the inflow rate thereof was 0.1 min/ml (space velocity 0.4 h$^{-1}$). It was found that 25 days or longer of operational stability could be maintained under these reaction conditions.

Figure 5:
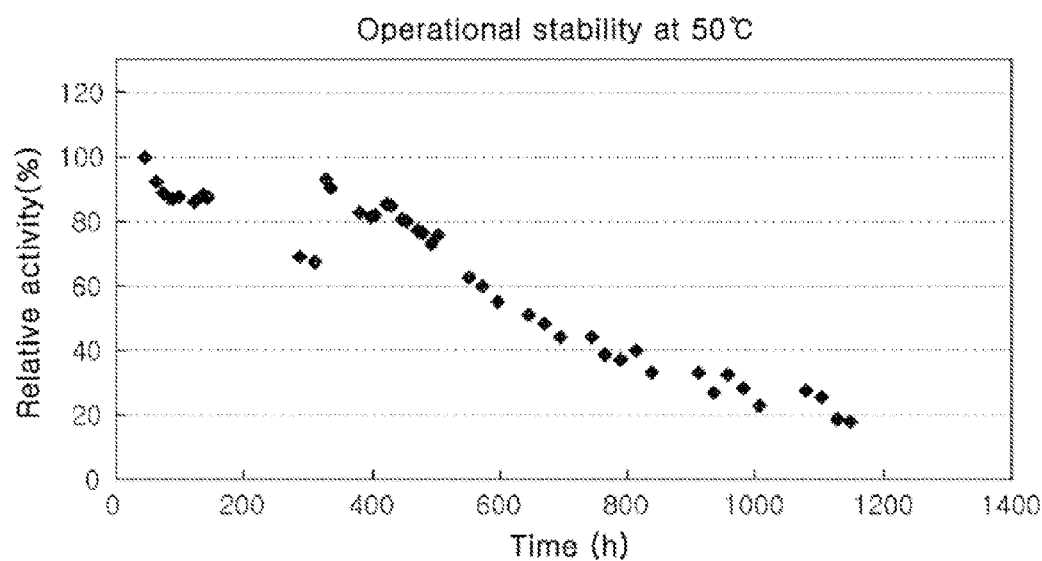
FIG. 5 illustrates the operational stability of an immobilization reactor at a reaction temperature of 50° C. for the method according to one embodiment of the present invention. A relative activity (%) means an activity relative to the activity at the time when the operation is initiated.

FIG. 5 shows the operational stability for the immobilized recombinant strain(s) at a reaction temperature of 50° C.

EXAMPLE 3

Figure 6A:
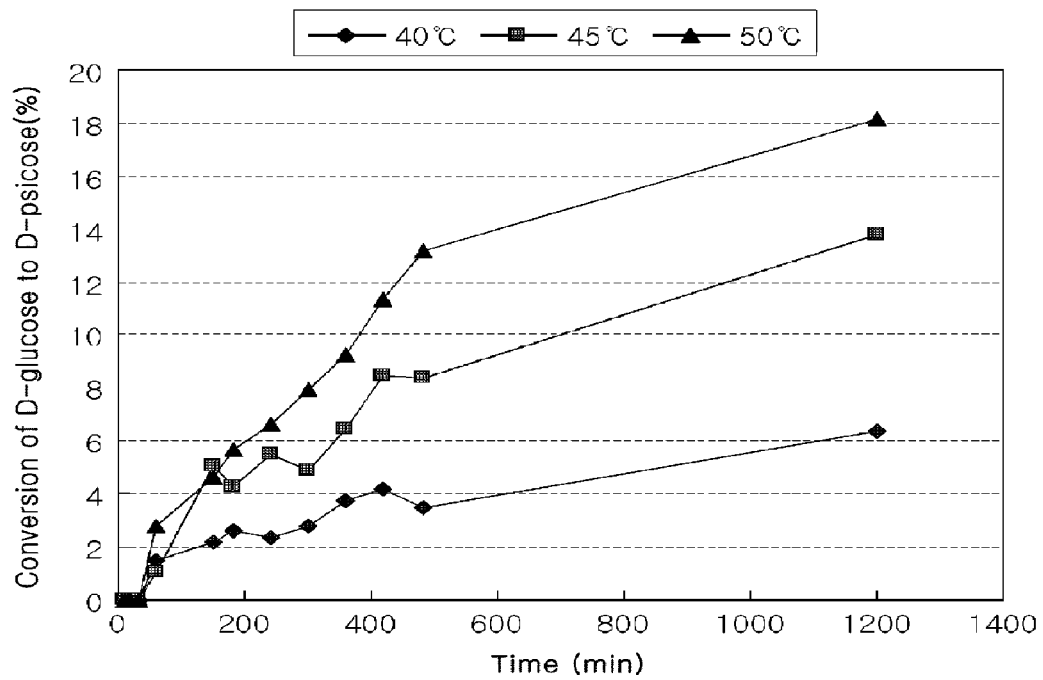
FIG. 6 illustrates % conversion of D-glucose to D-psicose by using the immobilized recombinant strain expressing the psicose-epimerase and the immobilized D-glucose isomerase under combined conditions of 100 g/L (6a), 300 g/L (6b), or 500 g/L (6c) of D-glucose, and 40° C., 45° C., or 50° C. of the reaction temperature for the method according to one embodiment of the present invention.
Figure 6B:
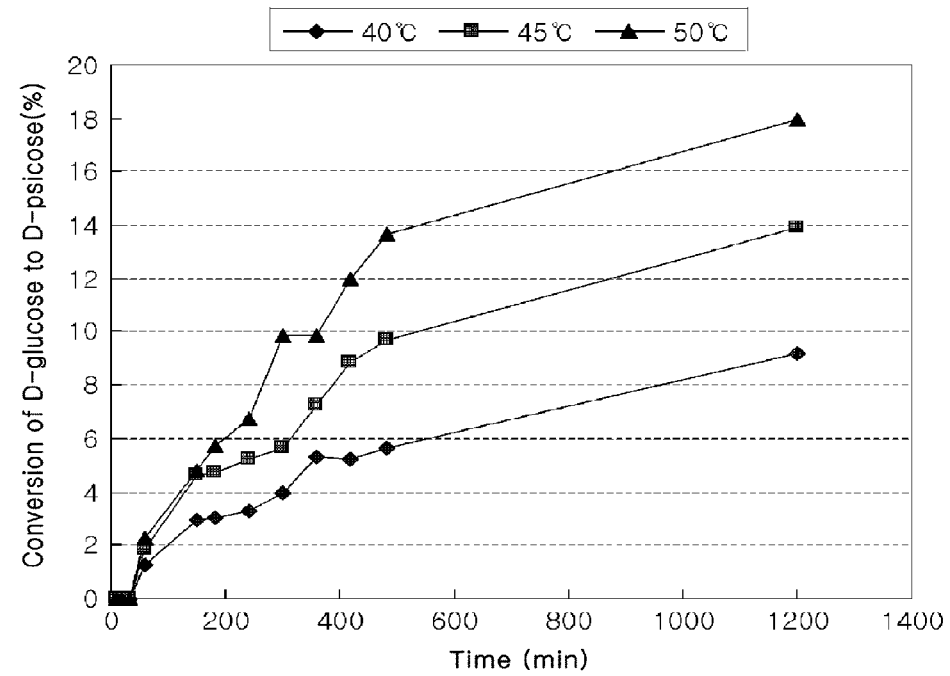
Figure 6C:
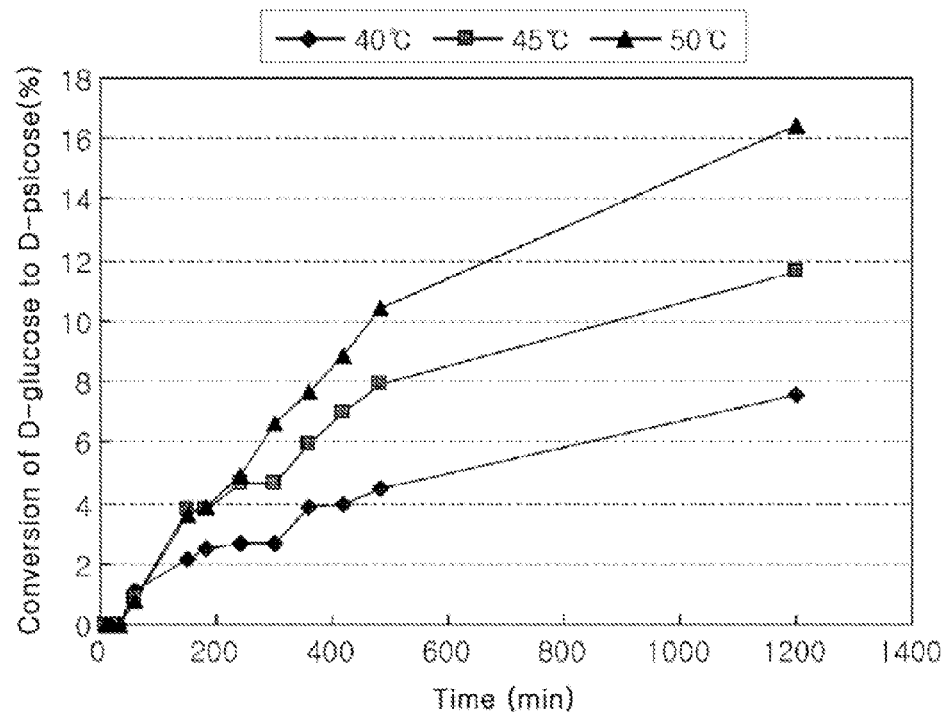

Preparation of D-psicose from D-glucose by Using the Immobilized Recombinant Strain/Enzyme (1) Productivity Depending on a Reaction Temperature and a D-Glucose Concentration The XK16 packed-bed columns (16 mm×20 mm, Amersham pharmacia) were packed with the recombinant strain immobilized onto sodium alginate in the above Example 2 and 10 g of the immobilized D-glucose isomerase (Novozymes, Denmark), respectively, followed by the measurement of % conversion of D-glucose to D-psicose. In order to determine the optimal reaction condition for the two mixed enzymes, the conversion reaction of D-glucose to D-psicose was conducted under combined conditions of 40° C., 45° C., or 50° C. of a reaction temperature, and 100 g/L, 300 g/L, or 500 g/L of D-glucose concentration. FIG. 6 shows % conversion of D-glucose to D-psicose depending on changes in the reaction temperature and the substrate concentration. According to FIGS. 6a to 6c, different from the epimerization reaction for D-psicose, the isomerization reaction for D-glucose was a temperature-dependent reaction. That is, the higher the reaction temperature the faster the conversion rate of D-glucose to D-psicose. It was found that this had effect on the productivity of D-psicose finally. The best conversion of D-glucose to D-fructose was achieved at a temperature of 50° C., and there was no significant difference in the reaction rate as the substrate concentration increased higher. These results demonstrate that it is possible to operate the immobilization reactor under the condition of a higher concentration of a substrate and to increase the productivity of D-psicose from D-glucose.

(2) Productivity Depending on an Inflow Rate of D-Glucose

Figure 7:
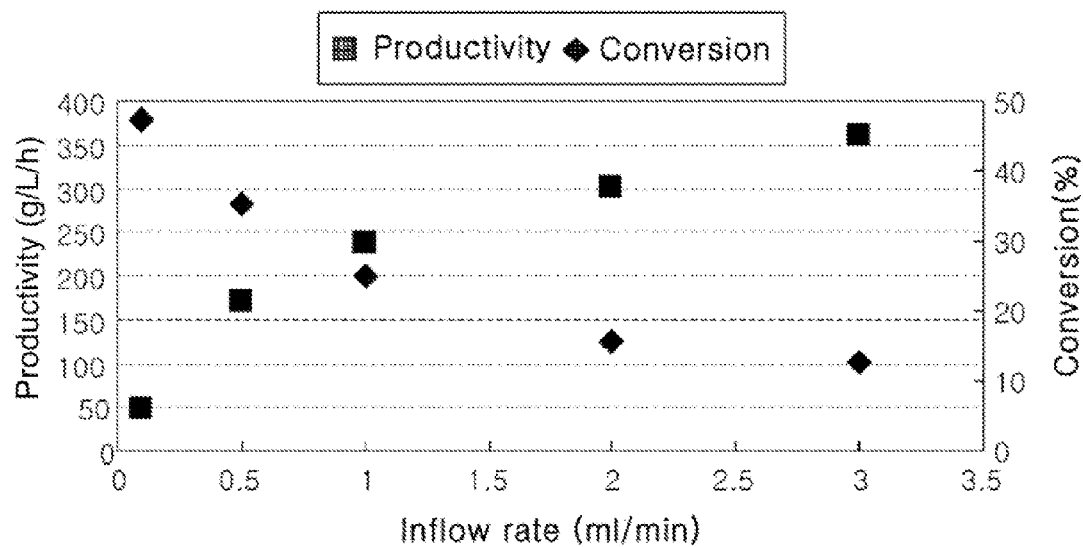
FIG. 7 illustrates the productivity of D-psicose depending on an inflow rate of D-glucose for the method according to one embodiment of the present invention.

The two packed-bed columns were packed with the immobilized recombinant strain including a psicose-epimerase and immobilized D-glucose isomerase, respectively, and the productivity of D-psicose was measured depending on an inflow rate of D-glucose. Based on the results of the above examples, the concentration of D-glucose and the reaction temperature were set at 300 g/L and 50° C., respectively. The productivity was measured by adjusting the inflow rate of D-fructose, a substrate to be 0.4, 1, 2, 4, and 8 h$^{-1}$ of space velocity (1/h). The results are shown below in Table 2 and FIG. 7.

TABLE 2

Productivity and % conversion depending on an inflow rate of D-glucose

| Inflow rate (ml/min) | D-glucose (g/l) | D-fructose (g/l) | Productivity (g/l/hr) | Conversion (%) |
|---|---|---|---|---|
| 4 | 281.465 | 31.136 | 374 | 9.96 |
| 3 | 278.849 | 40.042 | 360 | 12.56 |
| 2 | 267.061 | 50.196 | 301 | 15.82 |
| 1 | 238.615 | 78.854 | 237 | 24.84 |
| 0.5 | 207.168 | 113.081 | 170 | 35.31 |
| 0.1 | 172.826 | 155.850 | 47 | 47.42 |

The invention claimed is:

1. A method of preparing D-psicose from D-fructose by using a psicose-epimerase isolated from *Agrobacterium tumefaciens*, and expressed in a GRAS (generally accepted as safe) strain, wherein the GRAS strain is *Corynebacterium glutamicum* KCCM 11046, said method comprising steps of:
expressing the psicose-epimerase isolated from *Agrobacterium tumefaciens* in the GRAS strain; and
preparing D-psicose from D-fructose by using the expressed psicose-epimerase.

2. The method of claim 1, wherein the psicose-epimerase used in the preparation of D-psicose is contained in a culture of the GRAS strain or separated from the culture.

3. The method of claim 1, wherein the psicose-epimerase isolated from *Agrobacterium tumefaciens* has the amino acid sequence of SEQ ID NO: 1.

4. The method of claim 1, wherein the step of preparing D-psicose comprises the step of immobilizing the psicose-epimerase onto a carrier.

5. The method of claim 4, wherein the carrier is sodium alginate.

6. The method of claim 4, wherein the method further comprises the steps of packing a column with the carrier onto which the psicose-epimerase is immobilized and supplying the packed column with a D-fructose solution.

7. A method of preparing D-psicose from D-glucose, wherein psicose-epimerase is isolated from *Agrobacterium tumefaciens* and expressed in a GRAS (generally accepted as safe) strain, wherein the GRAS strain is *Corynebacterium glutamicum* KCCM 11046, comprising the step of immobilizing a psicose-epimerase and a D-glucose isomerase onto carriers.

8. The method of claim 7, wherein the expressed psicose-epimerase is contained in a culture of the GRAS strain or separated from the culture.

9. The method of claim 8, wherein the GRAS strain is a strain transformed with a recombinant vector including a gene encoding a psicose-epimerase.

10. The method of claim 8, wherein the psicose-epimerase has the amino acid sequence of SEQ ID NO: 1.

11. The method of claim 7, wherein the carrier is sodium alginate.

12. The method of claim 7, wherein the method further comprises the steps of packing a column with the carriers onto which the psicose-epimerase and the D-glucose isomerase are immobilized and supplying the carrier-packed column with a D-fructose solution.

13. The method of claim 12, wherein each of the carriers onto which the psicose-epimerase and the D-glucose isomerase are immobilized, respectively, is packed into a separate column, and the two columns are connected in communication with each other.

* * * * *

SEQUENCE LISTING

```
<160> NUMBER OF SEQ ID NOS: 10

<210> SEQ ID NO 1
<211> LENGTH: 289
<212> TYPE: PRT
<213> ORGANISM: Artificial Sequence
<220> FEATURE:
<223> OTHER INFORMATION: D-psicose 3-epimerase from Agrobacterium
      tumefaciens

<400> SEQUENCE: 1

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Ile Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Thr Trp
            100                 105                 110

Pro Ile Asp Tyr Ser Gln Pro Val Asp Lys Ala Gly Asp Tyr Ala Arg
        115                 120                 125
```

```
Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Tyr Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Tyr Leu Gly
        275                 280                 285

Gly

<210> SEQ ID NO 2
<211> LENGTH: 301
<212> TYPE: DNA
<213> ORGANISM: Artificial Sequence
<220> FEATURE:
<223> OTHER INFORMATION: CJ1 promoter

<400> SEQUENCE: 2
caccgcgggc ttattccatt acatggaatg accaggaatg cagggaatg cgacgaaatt      60 gactgtgtcg ggagcttctg atccgatgct gccaaccagg agagaaaata atgacatgtg    120
caggcacgct ggtgagctgg agatttatga tctcaagtac ctttttttctt gcactcgagg   180 gggctgagtg ccagaatggt tgctgacacc aggttgaggt tggtacacac tcaccaatcc    240
tgccgtcgcg ggcgcctgcg tggaacataa accttgagtg aaacccaatc taggagatta    300
a                                                                   301

<210> SEQ ID NO 3
<211> LENGTH: 285
<212> TYPE: DNA
<213> ORGANISM: Artificial Sequence
<220> FEATURE:
<223> OTHER INFORMATION: CJ2 promoter

<400> SEQUENCE: 3
aattccacca gacgttgttt agtaagtgcc cgaattctcg gttggtgcag ttgcttttcg     60
atgaatggga gaacctcgaa tacttccgcg tctctacttt ccggtacgtg ccacacagag    120
cagagcaatc ggtggaagag cacgacagat tagtagcgct tatcgaagcc caggcagaag   180
atttctacat cgaatcccaa gcccgcaacc accgcctgac aaccgcaacg acctaccgcc   240 aacgttttaaa ttccgaaaat catcacgaag aacaaggagt gcaca                  285

<210> SEQ ID NO 4
<211> LENGTH: 291
<212> TYPE: DNA
<213> ORGANISM: Artificial Sequence
```

```
<220> FEATURE:
<223> OTHER INFORMATION: CJ3 promoter

<400> SEQUENCE: 4
gctgcctaca tctggacttc tgacctgaag cgctcccaca acttcgcgca aaacgttgaa      60
gccggcatgg tctggttgaa ctccaacaac gtccgtgacc tgcgcacccc attcggtggc     120
gtcaaggcat ccggtctggg gcatgagggc ggctaccgct ccattgactt ctacaccgac     180
caacaggccg tacacatcaa cttaggcgaa gtccacaacc cagtcttcgg caagcaaacc     240
aactaattct ccctcatcca cactcccctt ttaacctcac taggagtcat c              291

<210> SEQ ID NO 5
<211> LENGTH: 312
<212> TYPE: DNA
<213> ORGANISM: Artificial sequence
<220> FEATURE:
<223> OTHER INFORMATION: CJ4 promoter

<400> SEQUENCE: 5
actgggaggg tagggtcac gctgaattag caggtcacat cctgttgctt gagctggccg       60
ttaccctcct aggatccgag atgattcttg tagaggacta cgtccgcac aaatcttccg     120 cgggatgctc aaatcaccct tagctggttt gaaaaatccg tggcataaat ctaggatcgt    180
gtaactggca cgaaaagaaa gcgtcatcgg cgcttgggaa catcttttta agatattcct    240
caagtgccgt gacatctgtc aaccccgtgg ctgcgagagt cgtagtcaca atgaagtcca    300
ggaggacata ca                                                          312

<210> SEQ ID NO 6
<211> LENGTH: 249
<212> TYPE: DNA
<213> ORGANISM: Artificial Sequence
<220> FEATURE:
<223> OTHER INFORMATION: CJ5 promoter

<400> SEQUENCE: 6
tcggacatat acggatttac ctgctgcaat cgcgccggcc cttgctcgaa attgcgtgaa     60
ttttagtctg attgtgttgg aatatccgca gaatgtgtgg gtttgctttt ataaatctgc    120
gcagtgtagg gaacctcggt actatcggca gtgtcggaga acttcctcg atataaatct    180 ttgaagtaat tctcccaggc aatagctttt gacgtactcc gcttcccaac tttttaggag   240
acaactacc                                                              249

<210> SEQ ID NO 7
<211> LENGTH: 332
<212> TYPE: DNA
<213> ORGANISM: Artificial Sequence
<220> FEATURE:
<223> OTHER INFORMATION: CJ6 promoter

<400> SEQUENCE: 7
ggcttcatcg tcgtctttga tccgatgcga gtccattaac ccaaactcct taaagcccgt     60
aaaacggggg tattccaaca cggttatcca cagtttaacc attattcggg ggtaatccta    120
acccaaatca ttacggaaac tccaatctgg ctcacaatat cctccatgat tctagggaca    180
cccaatcagg tgcacccgct tcctgcgaca acgagtcaaa ctcggcaaag ccctcaacct    240
gtcggtctag aatatatata ccgcccggtc tagtgttgtg gtgtacacta acgataaacc    300
aacaaagtta tctattaaga ggaggccatt tc                                   332
```

```
<210> SEQ ID NO 8
<211> LENGTH: 318
<212> TYPE: DNA
<213> ORGANISM: Artificial Sequence
<220> FEATURE:
<223> OTHER INFORMATION: CJ7 promoter

<400> SEQUENCE: 8
agaaacatcc cagcgctact aatagggagc gttgaccttc cttccacgga ccggtaatcg    60
gagtgcctaa aaccgcatgc ggcttaggct ccaagatagg ttctgcgcgg ccgggtaatg   120
catcttcttt agcaacaagt tgaggggtag gtgcaaataa gaacgacata gaaatcgtct   180
cctttctgtt tttaatcaac atacaccacc acctaaaaat tccccgacca gcaagttcac   240
agtattcggg cacaatatcg ttgccaaaat attgtttcgg aatatcatgg gatacgtacc   300
caacgaaagg aaacactc                                                  318

<210> SEQ ID NO 9
<211> LENGTH: 27
<212> TYPE: DNA
<213> ORGANISM: Artificial Sequence
<220> FEATURE:
<223> OTHER INFORMATION: Forward primer for D-psicose 3-epimerase

<400> SEQUENCE: 9
aaaactgcag atgaaacacg gcatcta                                         27

<210> SEQ ID NO 10
<211> LENGTH: 29
<212> TYPE: DNA
<213> ORGANISM: Artificial Sequence
<220> FEATURE:
<223> OTHER INFORMATION: Reverse primer for D-psicose 3-epimerase

<400> SEQUENCE: 10
ctagtctaga tcagccacca agaacgaag                                       29
```